(12) United States Patent
Eskaros et al.

(10) Patent No.: US 11,064,985 B2
(45) Date of Patent: Jul. 20, 2021

(54) TISSUE PLUG

(71) Applicant: W. L. Gore & Associates, Inc., Newark, DE (US)

(72) Inventors: Sherif A. Eskaros, Elkton, MD (US); John M. Herman, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 162 days.

(21) Appl. No.: 15/138,264

(22) Filed: Apr. 26, 2016

(65) Prior Publication Data

US 2016/0235393 A1 Aug. 18, 2016

Related U.S. Application Data

(62) Division of application No. 13/168,345, filed on Jun. 24, 2011, now abandoned.

(60) Provisional application No. 61/490,239, filed on May 26, 2011, provisional application No. 61/370,263, filed on Aug. 3, 2010.

(51) Int. Cl.
*A61B 17/00* (2006.01)
*A61B 17/22* (2006.01)

(52) U.S. Cl.
CPC ............ *A61B 17/0057* (2013.01); *A61B 2017/00004* (2013.01); *A61B 2017/00336* (2013.01); *A61B 2017/00575* (2013.01); *A61B 2017/00606* (2013.01); *A61B 2017/00619* (2013.01); *A61B 2017/00641* (2013.01); *A61B 2017/00654* (2013.01); *A61B 2017/00659* (2013.01); *A61B 2017/00898* (2013.01); *A61B 2017/00942* (2013.01); *A61B 2017/22038* (2013.01)

(58) Field of Classification Search
CPC ...... A61B 17/0057; A61B 2017/00575; A61B 2017/00606; A61B 2017/00654; A61B 2017/00659; A61B 2017/00641; A61B 2017/00592; A61B 2017/00597; A61B 2017/00619; A61B 2017/00623; A61B 2017/00898
See application file for complete search history.

(56) References Cited

U.S. PATENT DOCUMENTS

| 4,921,484 | A | * | 5/1990 | Hillstead | ............... | A61M 25/10 |
| | | | | | | 604/104 |
| 5,545,178 | A | | 8/1996 | Kensey | | |
| 5,700,277 | A | * | 12/1997 | Nash | ................. | A61B 17/0057 |
| | | | | | | 128/887 |
| 6,174,322 | B1 | | 1/2001 | Schneidt | | |
| 6,312,446 | B1 | | 11/2001 | Huebsch et al. | | |
| 7,485,087 | B2 | | 2/2009 | Burgard | | |
| 8,992,545 | B2 | | 3/2015 | Cahill | | |
| 2005/0049634 | A1 | | 3/2005 | Chopra | | |
| 2005/0085851 | A1 | | 4/2005 | Fiehler et al. | | |
| 2005/0149074 | A1 | * | 7/2005 | Pugsley, Jr. | ........ | A61B 17/0644 |
| | | | | | | 606/153 |

(Continued)

FOREIGN PATENT DOCUMENTS

| WO | WO 2006/078578 | 7/2006 |
| WO | WO 2009/070686 | 6/2009 |

(Continued)

*Primary Examiner* — Diane D Yabut
*Assistant Examiner* — Christian D Knauss

(57) ABSTRACT

Tissue plugs for occlusion of hollow anatomical structures and methods for their use are provided.

18 Claims, 12 Drawing Sheets

(56) References Cited

U.S. PATENT DOCUMENTS

| | | |
|---|---|---|
| 2005/0234509 A1* | 10/2005 | Widomski ......... A61B 17/0057 606/213 |
| 2007/0027550 A1 | 2/2007 | Farnsworth et al. |
| 2007/0031508 A1* | 2/2007 | Armstrong ......... A61B 17/0057 424/572 |
| 2007/0129757 A1 | 6/2007 | Armstrong |
| 2007/0198059 A1* | 8/2007 | Patel ..................... A61L 27/50 606/213 |
| 2007/0282430 A1* | 12/2007 | Thommen .......... A61B 17/0057 623/1.22 |
| 2008/0051831 A1 | 2/2008 | Deal et al. |
| 2008/0071310 A1* | 3/2008 | Hoffman ............ A61B 17/0057 606/215 |
| 2008/0245374 A1 | 10/2008 | Agnew |
| 2008/0249562 A1* | 10/2008 | Cahill ................ A61B 17/0057 606/215 |
| 2009/0054927 A1 | 2/2009 | Agnew |
| 2009/0069844 A1 | 3/2009 | Green et al. |
| 2009/0125119 A1 | 5/2009 | Obermiller et al. |
| 2010/0016885 A1* | 1/2010 | Eidenschink ........ A61B 1/3132 606/213 |
| 2010/0076463 A1* | 3/2010 | Mavani ............. A61B 17/0057 606/151 |
| 2010/0086578 A1 | 4/2010 | Nielsen et al. |
| 2011/0257674 A1* | 10/2011 | Evert ............... A61B 17/12109 606/194 |

FOREIGN PATENT DOCUMENTS

| WO | WO 95/29635 | 11/2009 |
|---|---|---|
| WO | WO 2009/146369 | 12/2009 |

* cited by examiner

TISSUE PLUG

FIELD OF THE INVENTION

The present invention relates to a medical device for occluding hollow anatomical structures and methods for use of these devices in occluding hollow anatomical structures.

BACKGROUND OF THE INVENTION

A variety of abnormal passages called fistula or fistulae can occur in the mammalian body. Fistulae may be caused by, for example, infection, congenital defects, inflammatory bowel diseases such as Crohn's disease, irradiation, trauma, cancer, childbirth, and surgical procedures. Fistulae may occur in the circulatory, respiratory, digestive, genitourinary, and musculoskeletal systems Examples include, but are not limited to, vesico-vaginal, urethro-vaginal, tracheo-esophageal, gastro-cutaneous, anorectal (ano-cutaneous), recto-vaginal, recto-vesical, recto-urethral and recto-prostatic fistulae. The most common fistulae occur from the intestine to an opening in the skin.

Various methods devices for repairing fistula have been described. The exact procedure and/or device will depend on the type of fistula being treated. One technique for treating fistulae involves the use of a plug-like device.

The Cook SIS Fistula Plug is manufactured from porcine small intestinal submucosa (SIS) and is intended for repair of anal, rectal, and enterocutaneous fistulae. The modified SIS Fistula Plug, also manufactured from porcine small intestinal submucosa, is supplied in a tapered configuration with a button to provide increased retention of the plug and improved blockage of the fistula.

The GORE BIO-A® Fistula Plug is intended for use in anorectal fistulae. This plug device has a three-dimensional disk with tube mesh design and is comprised of the synthetic bioabsorbable material polyglycolic acid:trimethylene carbonate (PGA:TMC).

Additional fistula plugs and/or devices for occluding hollow anatomical structures are described in for example, published U.S. Application Nos. 2008/0051831, 2008/0245374, 2009/0054927, 2009/0125119, and 2010/0086578, and U.S. Pat. No. 7,485,087.

SUMMARY OF THE INVENTION

The present invention provides medical devices for occlusion of hollow anatomical structures. It should be understood that devices of the present invention may be suitable for occlusion of any hollow anatomical structure such as a perforation, leak, tear, orifice, or aperture within the human body in need of treatment, which may be congenital or naturally occurring or as a result of injury, trauma, disease, etc. It should be further appreciated that the medical devices of the present invention may be used to occlude or plug a fistula or can be used in any other naturally occurring hollow anatomical structures, including but not limited to veins, arteries, coronary structures, pulmonary structures, tubular structures associated with reproductive organs, and the like. In one embodiment in the present invention, the device is used to treat gastrointestinal leaks and/or fistulae.

In one embodiment, devices of the present invention are used as a plug for a fistula or a gastrointestinal leak wherein the device comprises a first portion, an axial member which may be oriented through a fistula space and is connected to the first portion, and an occluding member which adjusts upon such axial portion to fill said space.

In another embodiment, the device comprises a first portion, such as an anchoring portion with a central aperture, an occluding member having a distal end and a proximal end and an interior and an exterior; the first portion positioned adjacent to the proximal end of the exterior of the occluding member; and an axial member attached to the interior distal end of the occluding member, wherein the axial member extends through the aperture of the anchoring portion. Upon pulling of the axial member in a direction further proximal to the anchoring portion, the distal end of the occluding member moves toward the proximal end of the occluding member thereby collapsing or bunching the occluding member. In an alternative embodiment, tensioning of the axial member with concurrent pushing of the occluding member will result in the collapsing or bunching effect sought. The resultant device, primarily by virtue of the occluding member, fills the hollow anatomical structure. In one embodiment the occluding member is a hollow tubular occluding member and the anchoring portion may be in the form of a planar anchoring means, such as a disk. The anchoring portion can thus serve to clamp or seal tissue, generally at the openings of the hollow anatomical structure, proximate to the anchoring portion.

Another aspect of the present invention relates to a method for occluding a hollow anatomical structure with the devices of the present invention. In one embodiment, the occluding device is positioned in a hollow anatomical structure so that the occluding member is inside the hollow anatomical structure and the first portion is at one opening of the hollow anatomical structure. The axial member of the device is then pulled in a direction away from, or more proximal to, the first portion, while the first portion is held in place upon the opening of the hollow anatomical structure, such that the distal end of the occluding member moves toward the proximal end of the occluding member, thereby collapsing or bunching the occluding member at least within the hollow anatomical structure. The device is thus able to fill the void created by the hollow anatomical structure and, optionally, seals tissue of the hollow anatomical structure near the first portion to secure the device in place.

DETAILED DESCRIPTION OF THE INVENTION

The present invention provides medical devices for occlusion of hollow anatomical structures. It should be understood that devices of the present invention may be suitable for occlusion of any hollow anatomical structure such as a perforation, leak, tear, or aperture within the human body in need of treatment, whether naturally occurring or as a result of injury, trauma, or disease, etc. It should be further appreciated that the medical devices of the present invention may be used to occlude or plug a fistula or can be used in any other hollow anatomical structures, including but not limited to veins, arteries, coronary structures, pulmonary structures, tubular structures associated with reproductive organs, and the like. In one embodiment in the present invention, the device is used to treat gastrointestinal (GI) leaks and/or fistulae.

In one embodiment, the device of the present invention comprises a first portion, an axial member which may be oriented through a fistula space and is connected to the first portion and at least one occluding member which adjusts upon such axial member to fill said space. The first portion may seal or close off the end of the tract of the hollow anatomical structure while the occluding member is able to effectively fill the tract of the hollow anatomical structure. This closing and/or sealing and filling of the void space, or packing of the tissue defect, achieved concurrently by the devices of the present invention may provide enhanced healing of the structure, such as a fistula or GI leak.

Figure 1:
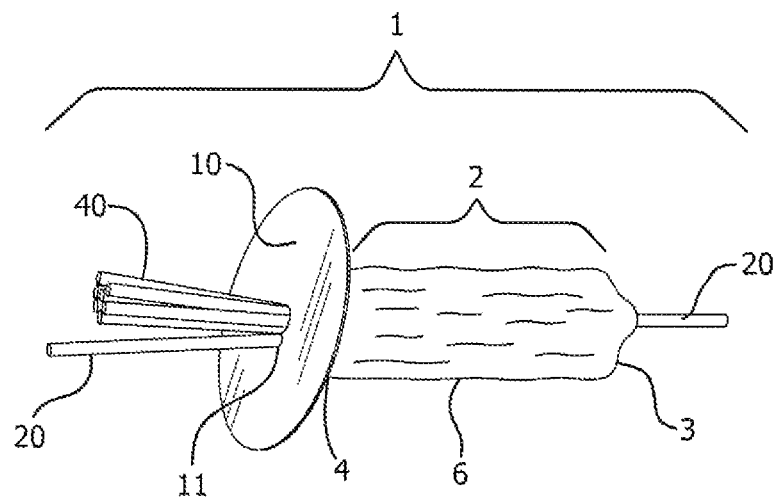
FIG. 1 provides a perspective view of an embodiment of a device of the present invention prior to deployment, FIG. 2 provides a perspective view of an embodiment of the device of the present invention after deployment via pulling of the axial member.

One embodiment of the device of the present invention is depicted in FIG. 1. As depicted therein, device 1 of the present invention may comprises a hollow occluding member 2 having a distal end 3 and proximal end 4, as well as an interior, and an exterior 6. The device may further comprise a first portion 10 with a central aperture 11 positioned adjacent to the proximal end 4 of the exterior 6 of the hollow occluding member 2 and connected to axial member 40. Axial member 40 is attached to the interior distal end 3 of hollow occluding member 2 and extends through the central aperture 11 of first portion 10.

Occluding member 2 may be in the form of a hollow tubular structure and should be sufficiently flexible, such that it can be collapsed or bunched up, however, it should have a certain resilience for holding its place within the hollow tissue structure or fistula. In many desired uses, a tubular structure is fabricated of a material that has loft to aid in space filling. Suitable designs which provide adequate loft and bunching may include but are not limited to, a web or mesh design, a foam, a sponge, or any other similar constructs.

Suitable materials for use in an occluding member of the present invention include any bioabsorbable material known in the art and may be synthetic or naturally occurring. Suitable bioabsorbable polymers for use in the occluding member of the present invention may include but are not limited to copolymers and homopolymers of poly(α-hydroxy esters), such as copolymers of poly(lactic-co-glycolic acid) (PLGA), poly(glycolic acid) (PGA), and polylactic acid) (PLA), trimethylene carbonate (TMC); copolymers of PLA and TMC (PLA:TMC), copolymers of PGA and TMC (PGA:TMC), and copolymers of PLGA and TMC; and combinations thereof. In one embodiment, the occluding member may be formed of a self-cohered bioabsorbable web material, such as that described in U.S. patent application Ser. No. 11/192,858 to Farnsworth et al., herein incorporated by reference in its entirety.

Occluding member 2 may conform to fill voids of varying sizes or irregular dimensions. Certain aspects of the occluding member may be altered to modify the extent to which it conforms to the inside of the hollow anatomical structure. For example, the use of low density material in construction of the occluding member can result in an occluding member that expands radially to a greater extent than a more dense material and more substantially fill a variety of fistulas or hollow tissue structures. The use of a highly porous material or structure may enhance cell ingrowth into the occluding member and promote healing. Similarly, the volume of material used in occluding member 2 may be varied to coincide with the size of the void space to be filled. In addition, the percentage of the volume of space to be filled may also vary. For instance, it may be advantageous to fill from about 10% to about 98% of the void volume with the occluding member. Occluding members that fill a higher percentage of the void volume of the fistula or hollow anatomical structure have greater contact with the tissue wall where the occluding member may ultimately serve as a tissue scaffold. In such instances, the tissue scaffold can provide for cellular penetration and cell ingrowth. Further, by varying the geometry of the occluding member along its length, it may be possible to control the points at which the tissue wall is in contact with the device or the amount of material that is positioned within the hollow anatomical structure void or tract. Alternatively, the cross sectional diameter of the occluding member may also be varied such that once the occluding member is collapsed or bunched, the diameter of the deployed device may vary along its length. Variations in stiffness of the occluding member material along its length may also lead to the desired variations in diameter of the deployed device. Such variations in diameter can be optimized to create predetermined contact regions. Such predetermined contact regions may advantageously enhance healing of the fistula, for instance, from the center outward. Any and all of the above variations in the occluding member may be employed individually or in combination when selecting an appropriate occluding member for use.

Further, when selecting the appropriate materials to be employed within the present invention, the texture, size of any fiber diameters where a fibrous material is utilized within the device, and/or roughness of the external surface of the device or any portion thereof, and in particular the occluding member, may be modified to provide debridement of the hollow tissue structure or fistula where desired. For example, a tighter mesh may provide more contact with the inner fistula wall. Materials with a more abrasive quality or enhanced surface roughness can also achieve the desired debridement. Fillers may be employed within or upon the surface of the materials of construction to enhance surface roughness of the device or portions thereof. Fillers that are suitable for this purpose include but are not limited to inorganic particles, metal particles, organic particles, and combinations thereof. Inorganic metal oxides and ceramic particles are of particular interest due to their biocompatibility and abrasive properties.

Additionally, the device or any portion thereof may be coated with, impregnated with, or otherwise incorporate additional components to enhance cell attachment or promote healing. In one embodiment, the device may deliver active agents to the hollow anatomical structure or fistula. Such actives can include but are not limited to pharmaceutical actives, hormones, growth factors, cells, and combinations thereof. Those actives of particular interest may include actives for suppressing or treating infection such as antibiotics, and actives for the reduction or prevention of pain or inflammation such as anesthetic agents and anti-inflammatory agents, Where active agents are incorporated into the present device, they can be provided as or within a coating on the device or any portion thereof, they can be directly incorporated into or admixed in the materials of construction to be used, they can be sandwiched or between fibers where present, or otherwise secured to or within the device by any means known in the art.

First portion 10 may be fixedly or slidably attached to axial member 40. First portion 10 may be in the form of a fixed point, such as a knot or bonded area of material, or any suitable anchoring member such as a substantially planar anchoring member, A substantially planar anchoring member may be a disk or sheet of material. When the first portion is in the form of a substantially planar anchoring member it should be large enough so that it overlaps the opening and stiff and/or thick enough to allow it not to be pulled through the opening. The first portion may comprise any biocompatible polymer material, whether bioabsarbabie or nonbioabsorbable, naturally occurring or synthetic, or combinations thereof. In one embodiment, the first portion 10 could comprise any biocompatible material that is capable of forming a substantially planar member. Suitable bioabsorbable materials may include but are not limited to copolymers and homopolymers of poly(α-hydroxy esters), such as copolymers of poly(lactic-co-glycolic acid) (PLGA), poly(glycolic acid) (PGA), and poly(lactic acid) (PLA); trimethylene carbonate (TMC); copolymers of PLA and TMC (PLA:TMC), copolymers of PGA and TMC (PGA:TMC) and copolymers of PLGA and TMC; and combinations thereof. Suitable nonbioabsorbable materials for use in the first portion 10 may include but are not limited to nylon, polypropylene, polyethylene, polyethylene terephthalate, polytetrafluoroethylene (PTFE), expanded polytetrafluoroethylene (ePTFE) and combinations thereof.

Figure 6:
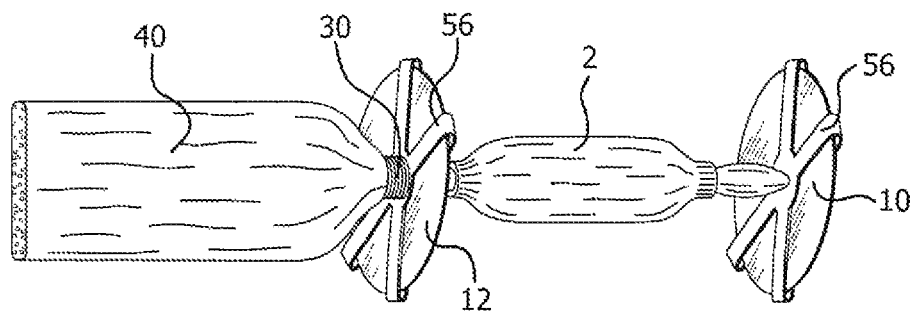
FIG. 6 provides a perspective view of another embodiment of the present invention, further comprising a second portion in the form of a planar anchoring member.
Figure 7:
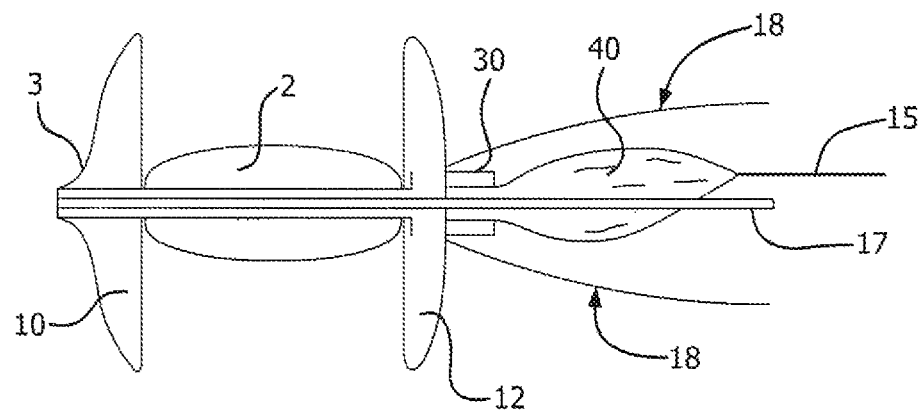
FIG. 7 is a perspective view of yet another embodiment of the present invention, further comprising an additional axial member in the form of a push rod to aid in redeployment of device.

In some embodiments, it may be desirable to seal the occluding member within the tract of the hollow anatomical structure, such as a fistula, by sealing both ends of the fistula tract. This can be done in a variety of ways. The occluding member itself may be designed such that, upon deployment, the distal end of the occluding member may form a wide seal at the opposite end of the fistula. Alternatively, as depicted in FIGS. 6 and 7, the devices of the present invention may comprise a first portion 10 and a second portion 12 positioned adjacent the distal end and proximal ends of the occluding member 2 along axial member 40. Similar to the first portion, the second portion may be in the form of a fixed point, such as a knot of material, or any suitable anchoring member, such as a substantially planar anchoring member. Where the second portion is a substantially planar anchoring member, a disk or sheet of material may be appropriate. Where a first and second portion are both employed in the devices of the present invention, one portion is generally fixedly connected to the axial member while the other portion is generally slidably or moveably connected to the axial member. In one embodiment, however, a second axial member may be employed and one axial member may be slidably or fixedly attached to both a first and second portion. The second portion may comprise a bioabsorbable or nonbioabsorbable, natural or synthetic material. Where both a first portion and a second portion are present, the first and second portions may comprise the same or different materials. For instance, the first portion may be bioabsorbable while the second portion is nonbioabsorbable. This may be advantageous, for example, when the bioabsorbable portion is positioned outside the hollow anatomical structure, such as outside the gastrointestinal tract, and the nonbioabsorbable portion may be located within the hollow anatomical tissue site, such as within the gastrointestinal tract. Alternatively, the first portion may be a bioabsorbable material and the second portion may be a different bioabsorbable material. Further, it may be advantageous to have a first portion and a second portion with varying degradation or detachment rates. For example, where one portion is located within the gastrointestinal tract, that portion may be designed to detach from the device at a faster rate than the other portion which may be designed to stay in place and maintain rigidity longer. Such detachment can be designed via any suitable means within either the axial member or the first or second portions.

Figure 4:
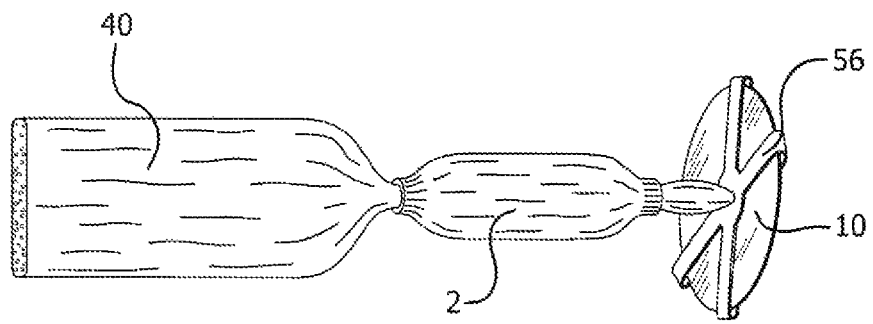
FIG. 4 provides a perspective view of a device of the present invention in a partially deployed state.
Figure 5:
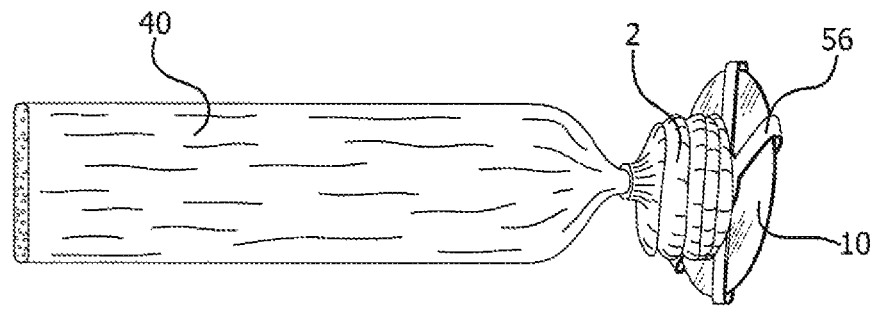
FIG. 5 provides a perspective view of a device of the present invention in a deployed state.

As described above, the device also comprises an axial member 40. As depicted in FIG. 1, the axial member 40 may be attached to the interior distal end 3 of the hollow occluding member 2. Alternatively, as depicted in FIG. 4, the axial member 40 may be attached to the first portion 10, with occluding member 2 slidably positioned thereon.

Figure 2:
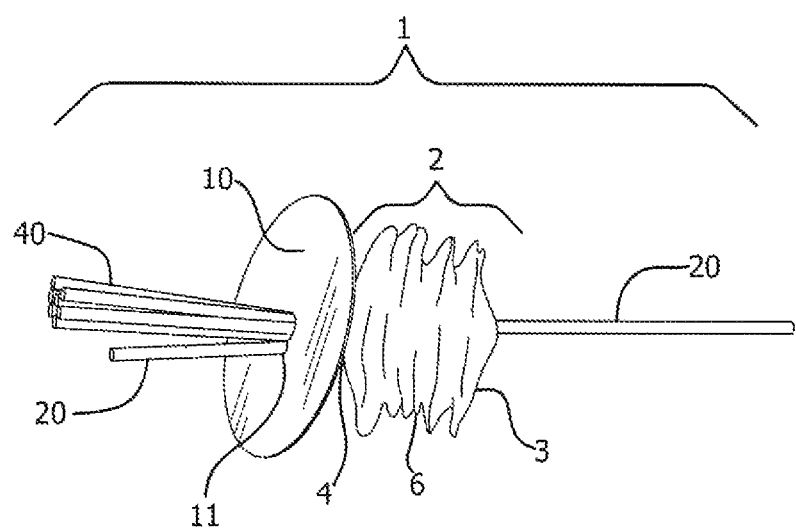

As shown in FIG. 2, when the axial member 40 is pulled in a direction away from, in this instance further proximal to, the first portion 10 and occluding member 2, the distal end 3 of the occluding member 2 moves toward the proximal end 4 of the occluding member 2 causing the occluding member 2 to collapse or bunch up. When the device of the present invention is positioned in a hollow anatomical structure such as a fistula, the device is positioned so that the occluding member is inside the fistula tract and the first portion is at the internal opening of the fistula. Once positioned, pulling of the axial member results in collapsing or bunching of the occluding member which plugs the fistula and clamps the tissue near the first portion, thereby fixing the device in place. Where a second portion is present, the external opening of the fistula can likewise be treated, Optionally, this configuration may be used to effectively seal the fistula tract in situations where sealing would prove advantageous.

Figure 3A:
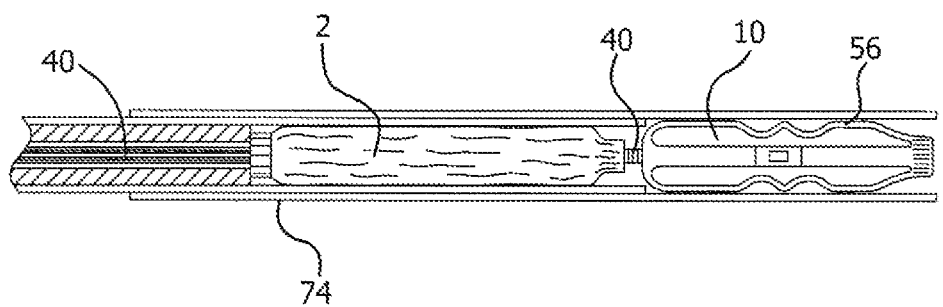
FIGS. 3a and 3b provide a perspective view of an alternate embodiment of the device packaged within a tube or catheter for delivery into a fistula.
Figure 3B:
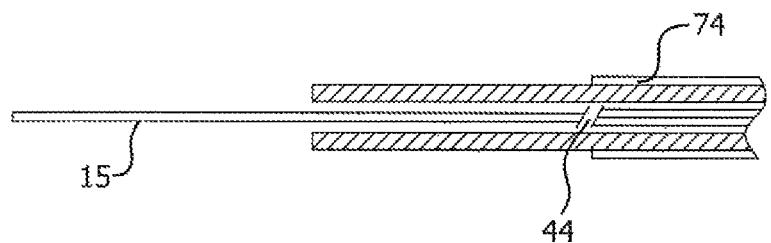

The axial member may likewise be modified by the addition of a pull cord 15 as depicted in FIG. 3b. A pull cord can be useful to lengthen the portion of the device that is available for grasping by the surgeon while the device is positioned within a catheter 74, for instance, prior to placement. The pull cord 15 may be attached to the axial member via any attachment means 44. Attachment means may include a knot or other tying connection formed from the material of the pull cord or axial member, a welded connection, an adhesive bond, a crimping mechanism, etc. Alternatively, the distal end of the axial member may comprise a self bonded end portion which may serve as an anchor for a pull cord that can be threaded through the axial member at a point proximal to the axial member end portion. In that embodiment, the pull cord itself would not be immovably fixed to the axial member but could form a sliding loop that can be cut or opened for easy removal from the device by pulling.

Once positioned, axial member 40 or pull cord 15 of the device may extend from within the fistula to beyond the fistula tract and into adjacent space. As such, the axial member or pull cord may act to wick fluids effectively from the fistula space thereby draining the fistula during the healing process, Advantageously, where a bioabsorbable axial member or pull cord is employed, the axial member or pull cord may serve to drain the fistula during healing and subsequently be resorbed into the body, eliminating the need for any secondary surgery required for removal of the device. Although it should be understood that both the axial member and/or the pull cord can be formed of any bioabsorbable or nonbioabsorbable, natural or synthetic material.

In some instances, it may be desirable that the device be able to be removed and redeployed, for instance in situations where placement into the fistula or hollow anatomical structure is initially improper or incorrectly placed. In one embodiment, affixing an additional axial member to the proximal end of the device would allow for the occluding member to be axially stretched if necessary to its original length and repositioned. Alternatively, as shown in FIG. 7, an additional axial member, such as a push rod 17 may be provided which is in communication with the distal end 3 of the occluding member 2 and which could be used to push the distal end 3 of the occluding device 2 away from the proximal end 4 after a failed delivery attempt in order to stretch the occluding member 2 back to its original length, thereby allowing for redeployment via axial member 40.

The device of the present invention may further comprise a guidewire 20 to facilitate positioning of the device in a hollow anatomical structure. In one embodiment, as depicted in FIGS. 1 and 2, the guidewire 20 is positioned adjacent to axial member 40 and extends through aperture 11 of first portion 10, continues through the interior of the occluding member 2, and passes out the distal end 3 of the occluding member.

In an alternate embodiment, the device has a lumen running through it that allows for the passage of a guidewire. This embodiment allows for maintenance of the guidewire position throughout the procedure and may provide a degree of self centering of the device within the fistula tract. Any hole which remains after the guidewire is removed should be sealed, which can be accomplished by any suitable means.

In one embodiment where deployment over a guidewire is contemplated, the device may be contained within a protective sleeve or sheath until deployed. In one embodiment, a smooth sheath outer surface may be desirable to achieve initial placement within the body and to avoid injury to the surrounding bodily tissues, however, subsequently, a coarser interface with the fistula tissues may be desired. One configuration providing this two-fold effect involves an inner delivery sheath and an outer delivery sheath whereby the surfaces have coarser and smoother textures, respectively. Once inserted into the fistula, the outer smooth-surfaced sheath may be removed, and the coarser-surfaced inner sheath may be used to enhance contact between the device and the fistula inner surface through debridement of adjacent tissues. The inner delivery sheath may also be used to supplement the collapsing of the occluding member. The roughness of the sheath surface may be enhanced by any suitable mechanical, chemical, or material means. In one embodiment, the sheath may be comprised of a polymer containing abrasive filler particles. Fillers useful for this purpose include but are not limited to inorganic particles, metal particles, organic particles, and combinations thereof. Alternatively, the surface of an otherwise smooth sheath may be roughened by mechanical means such as mild sand-blasting or sanding. Once the desired debridement of the fistula tissues is completed, the inner delivery sheath is removed and final placement and deployment of the device is commenced.

Devices of the present invention may further comprise one or more reinforcement elements 56 that are associated with the first or second planar anchoring members as depicted in FIG. 4. Said reinforcement elements may comprise any reinforcement structure or material that provides support to the first portion and/or second portion. In one embodiment, the reinforcement elements may take the form of struts. The reinforcement elements may be attached to or provide support to the first portion and/or second portion in any manner. For example, struts may be folded or bent to encompass the first portion therein or, alternatively, struts may be bonded or adhered to one surface of the first portion only. When the first portion and/or second portion are in the form of a planar anchoring member, the reinforcing elements effectively increase the force necessary to dislodge the device after deployment. The reinforcing elements also are useful in preventing the planar anchoring member(s) from folding onto itself during placement and deployment. The reinforcing elements may further help reduce migration of the device within the fistula.

In one embodiment, where the first and/or second portions are planar anchoring members, ribs or struts having a rigidity greater than that of the planar anchoring member(s) may provide suitable reinforcement. Such ribs or struts may be oriented along the longitudinal axis of the device when in an undeployed configuration and subsequently become radially oriented substantially perpendicular to the longitudinal axis after deployment. Such ribs or struts may further assist in deployment of the occluding member.

Figure 15A:
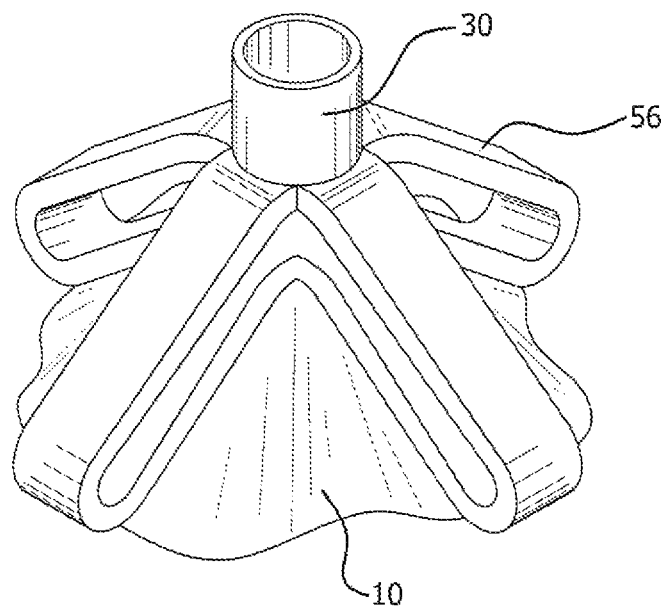
FIGS. 15a and 15b are perspective views of one embodiment of the present invention where the first portion is a planar anchoring member reinforced with a convex strut and collar mechanism.
Figure 15B:
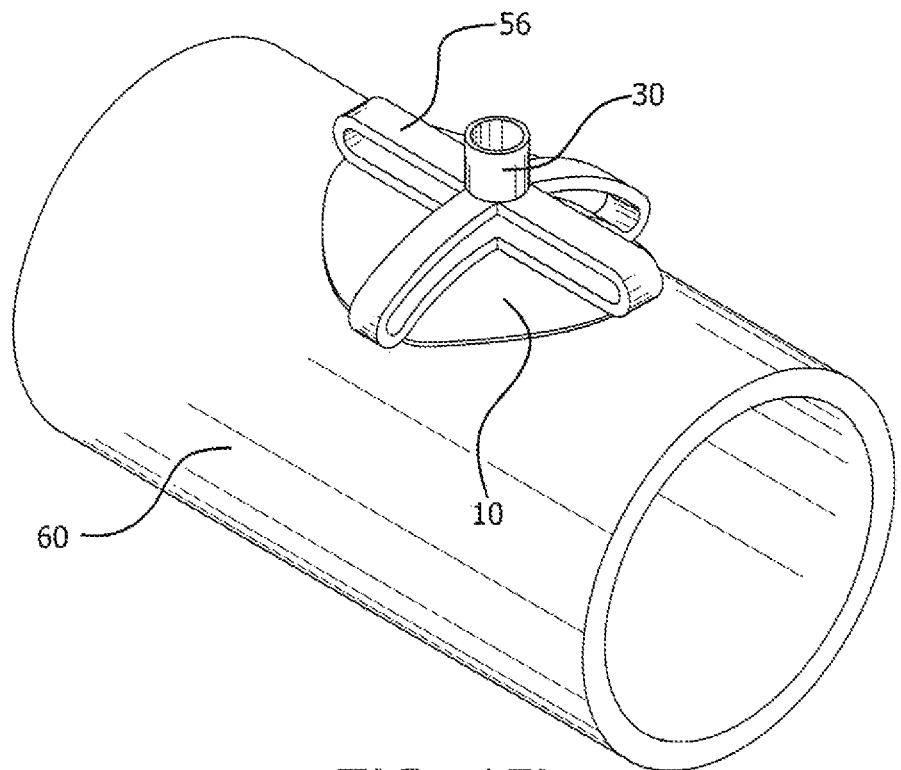

In yet another embodiment, the reinforcing elements may be oriented substantially circumferentially to enhance the optional seal formed between the first portion and the fistula opening. In another embodiment the reinforced planar anchoring member is anatomically shaped upon deployment, by virtue of struts that are designed to conform to various three dimensional shapes, Such devices may better conform to a fistula or wound site if the wound site is located on a portion of the body where the planar end portions may not seal sufficiently but where sealing is desired. Combinations and variations of the size or length, number of, orientation, or configuration of these reinforcing elements may be used to create a three dimensional form upon deployment of the device as shown in FIGS. 15a and 15b. In this embodiment, reinforcing elements in the form of struts 56 are affixed on one side of a first or second portion and comprise portions of differing lengths. Upon deployment of the device, struts 56 do not extend to be substantially linear but rather curve to maintain the first portion 10 in a generally concave shape.

Devices of the present invention may further comprise a collar to assist in controlling movement of the various components of the devices of the present invention. In one embodiment, the collar will be integrally formed from the reinforcing elements and protrude therefrom in a generally perpendicular manner. Collars for use in the present invention comprise a central aperture that allows for passage of an axial member and/or pull cord there through.

Figure 14A:
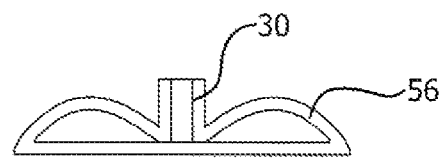
FIG. 14a is a side view of a first portion of a device subsequent to deployment, wherein the first portion is a disk and where the device further comprises a reinforcing element in the form of a strut structure located on the disk wherein the struts are configured such that the portion of the strut located on one side of the first portion is longer than the portion of the strut located on the other side of the first portion.
Figure 14B:
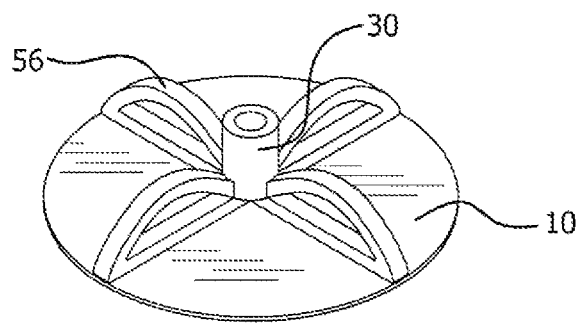
FIG. 14b is a perspective view of the deployed first portion of FIG. 14a where in the struts structure is located on one side of the first portion.
Figure 14C:
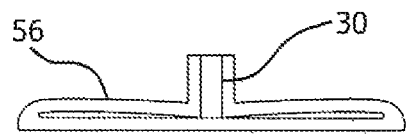
FIG. 14c is a side view of the deployed first portion of FIG. 13.

FIG. 14a shows an embodiment of asymmetric reinforcing elements in which the portion of the reinforcing elements or struts 56 on the collar 30 side is longer than the portion of the strut on the opposite side. This embodiment is particularly useful to prevent inversion of the first portion 10, shown in FIG. 14b. FIG. 14c shows an embodiment in which both portions of the reinforcing elements 66 have approximately equal lengths. Substantially similar length portions of the reinforcing elements result in the device having a generally flat cross-section as shown in FIG. 14c.

Figure 8:
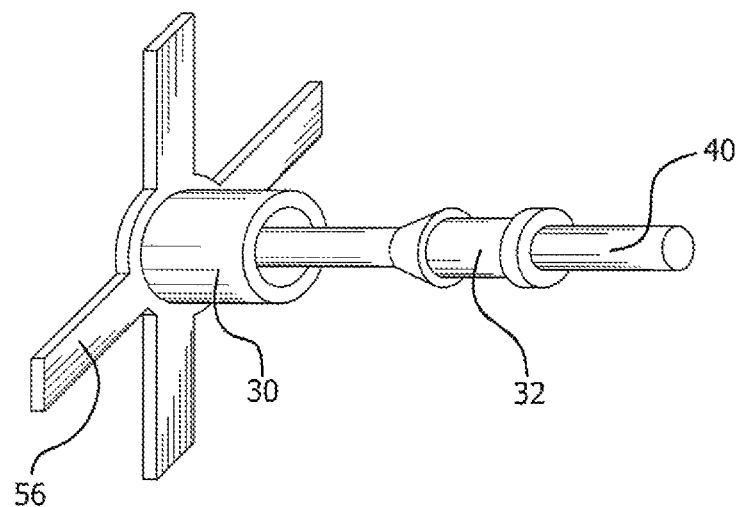
FIG. 8 is a perspective view of a collar and snap lock means suitable for use in the devices of the present invention for securing the position of the axial member post deployment.
Figure 9:
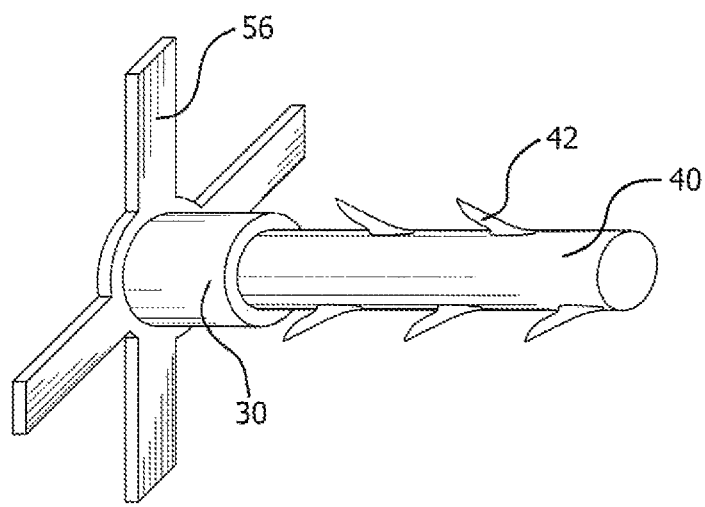
FIG. 9 is a perspective view of an alternative locking means suitable for use in the devices of the present invention wherein a barbed axial member is employed to provide unidirectional securing of the axial member post deployment.
Figure 10:
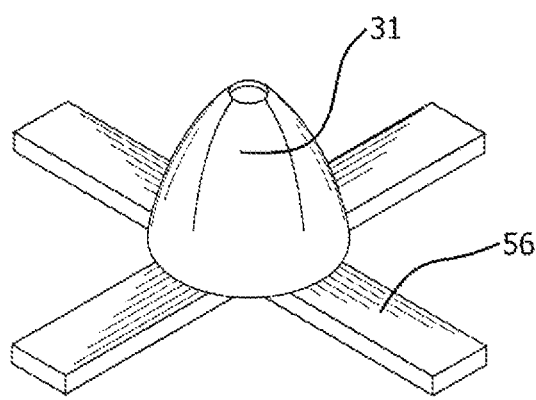
FIG. 10 is a perspective view of a collar suitable for use in the present invention which incorporates in integral locking means in the form of individual tangs for securing the axial member in place.
Figure 11A:
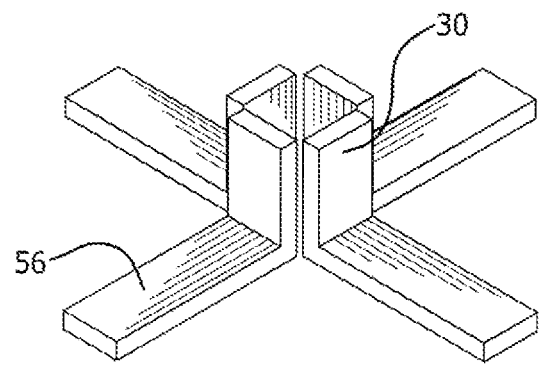
FIGS. 11a and 11b are perspective views of a collar formed from reinforcing elements and a separate elastomeric locking component which compresses the collar to secure the position of an axial member passing there through post deployment.
Figure 11B:
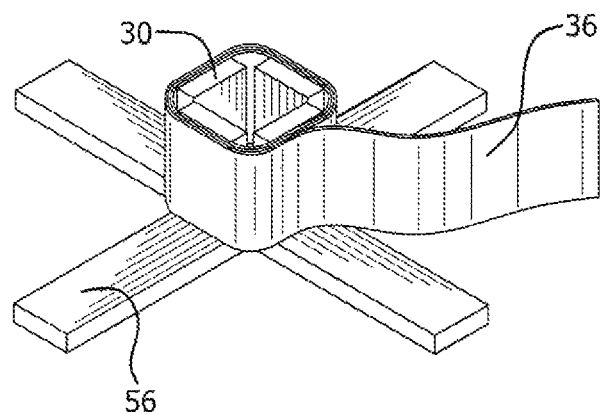
Figure 12:
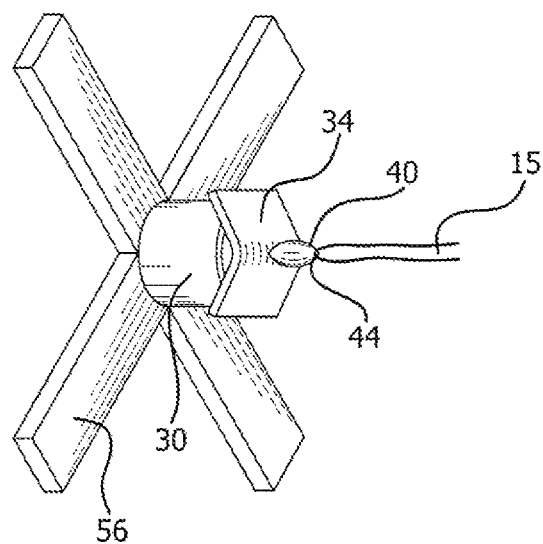
FIG. 12 depicts a locking clip that may be attached to the axial member at a predetermined point and upon passing through a collar, expands to prevent the locking clip and axial member from sliding back through the collar.
Figure 13:
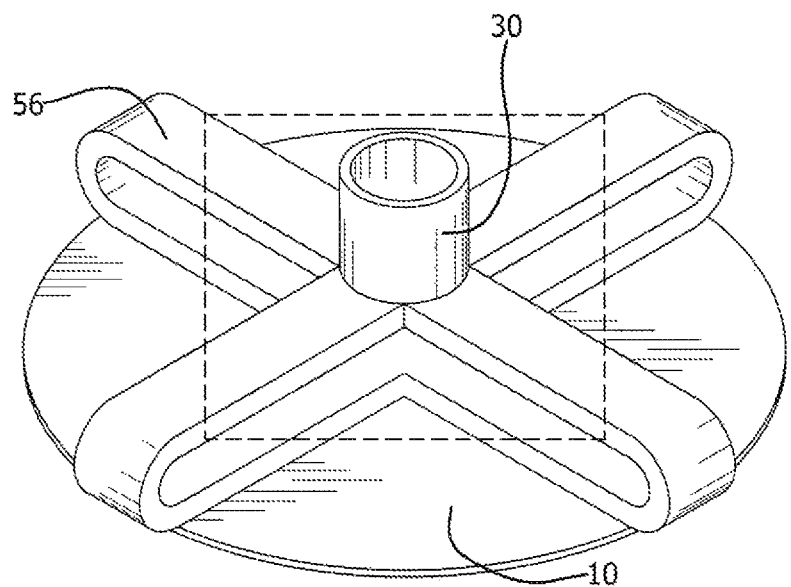
FIG. 13 is a perspective view of a first portion of a device subsequent to deployment, wherein the first portion is a disk and where the device further comprises a reinforcing element in the form of a strut structure with struts of substantially similar length.

Collars suitable for inclusion in the present invention are intended to reduce the freedom of movement of any components which may move or slide along the axial member during delivery or deployment, such as the distal end of the occluding member, and/or to reduce any movement that may lead to partial or improper deployment. This function may be accomplished for example by varying the relative friction between the axial member and the collar such that as the distal end of the occluding member slides along the axial member, the friction increases, effectively locking the distal end of the occluding member in place when fully deployed. Alternatively, chemical or mechanical locking means may be employed to achieve the locking of any movable components. For example, a two part adhesive may be employed which is activated upon comingling of the first part and second part to secure the location of the movable components relative to one another. Alternatively, magnetic means may be employed to secure components relative to one another. In an alternative embodiment, a snap lock arrangement may be provided as in FIG. 8 where a locking component is secured to the axial member at a predetermined location. As the axial member 40 passes through the collar 30, a tapered locking component 32 is configured to mate with the collar and snap into place, thus eliminating further movement of the axial member. In another example, barbs may be incorporated into the collar and/or along the axial member in a way that limits movement of the axial member once deployed. FIG. 9 illustrates one example wherein the axial member further comprises a barb mechanism. In FIG. 9, the axial member 40 comprises barbs 42 which can provide for unidirectional locking of the axial member by engagement with an optional collar 30. Alternatively, barb-type elements may be integral to and protrude from the interior portion of an optional locking collar itself to aid in locking an axial member therein. FIG. 10 depicts another potential locking mechanism that may be suitable for use in the present invention, wherein locking collar 31 comprises a plurality of tangs which operate to secure an axial member therein as it passes through the locking cap preventing slippage back through the locking collar. FIGS. 11a and 11b depict yet another embodiment wherein the collar 30 is integrally formed from the ends of the reinforcing elements or struts 56 and projects perpendicularly therefrom. A separate elastomeric element 36 can be introduced to hold collar 30 taught and provide tension on any axial member passing there through, again preventing slippage of the axial member once in place. FIG. 12 depicts yet another optional collar 30 with locking clip 34 which is attached to the axial member 40 at a predetermined location and designed to pass through collar 30. Axial member 40 is pulled, via pull cord 15 through the collar 30 during deployment. Once the locking clip has exited the collar, the clip opens in a butterfly motion or expands to prevent locking clip 34 and attached axial member 40 from sliding back through the collar 30. Any other suitable interlocking means may also be used. Depending on the locking mechanism selected, the collar may be made from a range of materials including metals, plastics, elastomers, rubbers, ceramics, or combinations thereof, Rubber and elastomeric collars may be designed to provide any desired amount of slippage and/or sliding along the axial member.

The present invention also provides methods for occluding a hollow anatomical tissue structure such as a fistula with these medical devices. In these methods, the device is positioned in the hollow anatomical tissue structure so that the occluding member or the device is positioned inside the hollow anatomical tissue structure and the first portion is an opening of the hollow tissue structure. In one embodiment the first portion is a planar anchoring member, such as a disk, and positioned at the internal opening of the fistula for tissue to be clamped between the occluding member and the disk. It should be understood, however, that the disk may be placed at the internal opening or the external opening of the hollow anatomical tissue structure. Alternatively where both first and second portions are employed, a first portion, such as a planar anchoring member, may be placed at one opening of the fistula and a second portion, such as a second planar anchoring member, may be positioned at the opposite opening of the fistula tract. Means for delivery of the device is selected based upon the position of the hollow anatomical tissue structure to be occluded and may be performed in a variety of ways. In one embodiment, the device is delivered to the site of the hollow anatomical tissue structure to be occluded endoscopically using, for example, an endoluminal catheter. Thus, for occlusion of a tracheo-esophageal fistula, for example, the device is delivered endoscopically via the trachea or the esophagus.

By providing a catheter having a roughened outer surface, debridement of the hollow anatomical structure may be accomplished via the delivery process. The roughness of the catheter surface may be enhanced by any suitable mechanical, chemical, or material means. For example, the outermost portion of the catheter may be comprised of a polymer containing abrasive filler particles. Fillers useful for this purpose include but are not limited to inorganic particles, metal particles, organic particles, and combinations thereof. Inorganic metal oxide and ceramic particles are of particular interest due to their biocompatibility and abrasive properties. Another embodiment may employ mechanical means to increase the catheter surface roughness, such as but not limited to mild sand-blasting or sanding.

Once positioned, the axial member of the device is pulled in a direction more proximal from the first portion such that the distal end of the occluding member moves toward the proximal end of the occluding member, thereby filling the hollow anatomical structure and clamping tissue of the hollow anatomical structure near the first portion to lodge the device FIG. 16 shows a series of images depicting a typical device deployment to plug an anastomotic dehiscence 62 in a GI tract extraluminal surface 60.

Figure 16A:
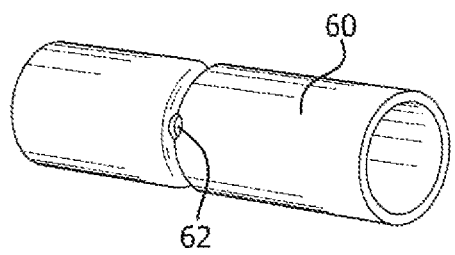
FIGS. 16a through 16h depict the typical steps for deployment of one embodiment of the present invention.
Figure 16B:
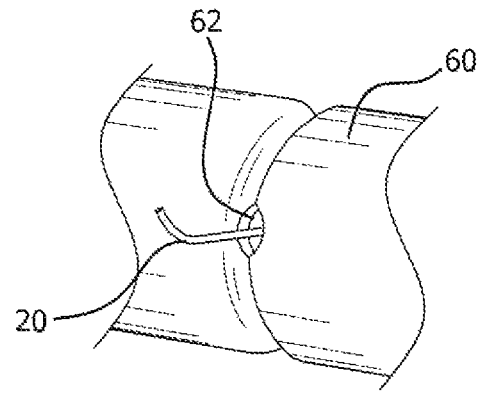
Figure 16C:
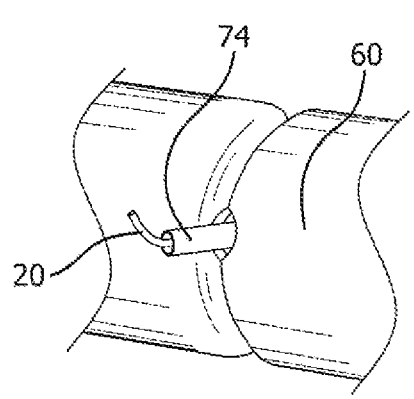
Figure 16D:
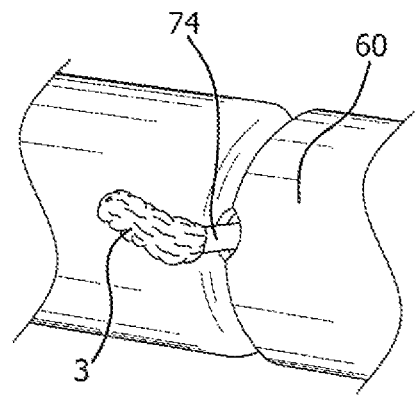
Figure 16E:
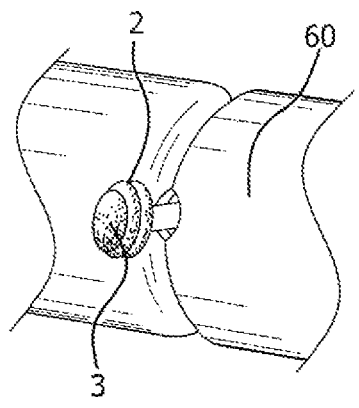
Figure 16F:
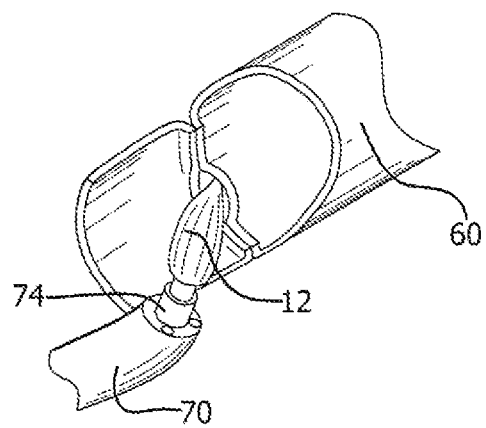
Figure 16G:
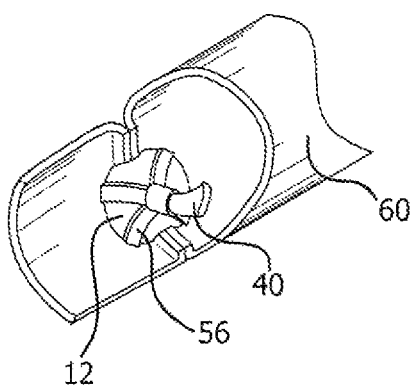
Figure 16H:
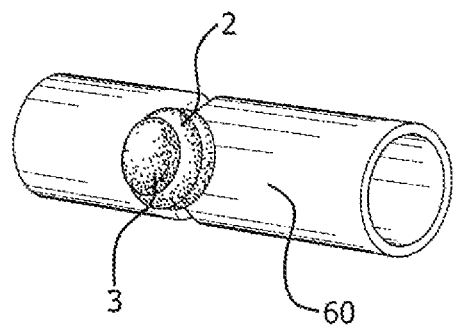

FIG. 16a shows an extraluminal surface 60 of the GI tract having an anastomotic dehiscence 62. Initial device deployment typically begins with the endoscopic placement of guidewire 20 from within the GI tract through anastomotic dehiscence 62 and extending beyond extraluminal surface 60 as shown in FIG. 16b. Once the guidewire 20 is positioned, catheter 74 is fed along guidewire 20 until it passes through anastomotic dehiscence 62 and extends beyond the tract extraluminal surface (FIG. 16c). Distal end 3 of the device is then pushed through catheter 74 until sufficient material to create a plug is present (FIG. 16d). Catheter 74 is then partially withdrawn leaving sufficient material of occluding member 2 outside the extraluminal surface 60 (FIG. 16e), On the inside of the GI tract, endoscope 70 containing partially retracted catheter 74 is positioned so that first portion 10 has room to deploy (FIG. 16f), First portion 10 is deployed via a push rod or inner delivery tube that is positioned within catheter 74 that extends to the proximal end of endoscope 70. Once freed from catheter 74, the push rod or inner delivery tube (not shown), may be used to push first portion 10 against the inner surface of the GI tract while axial member 40 is pulled via the pull cord from the proximal end of the endoscope. As the first portion 10 is squeezed against the inner GI tract surface, struts 56 expand outward, thereby positioning first portion 10 across anastomotic dehiscence 62 (FIG. 16g). FIG. 16h shows the extraluminal surface 60 with the collapsed occluding member 2 plugging anastomotic dehiscence 62.

Because the device of the present invention can be prepared completely from bioabsorbable materials, the device and methods of the present invention may provide a non-permanent means for occluding a hollow anatomical structure such as a fistula, Where the device is solely constructed of bioabsorbable materials, no permanent implant or prosthetic material remains in the body and no additional fixation means are required; the device and methods of the present invention significantly reduce the chance of infection, erosion and/or long-term complications. Further, no second procedure to remove the device, or parts of the device, would be required.

In addition, the healing process as well as direction of healing may be affected by the choice of materials as well as the design of the device. For example, materials may be used having differing rates of resorption. When these differing bioabsorbable materials are used to create a gradient of resorption rates, the direction of healing and resorption may be controllable. Resorption of the device could be controlled, for example, by varying the density of different portions of the device, selecting materials having different densities for various portions of the device, varying the fiber diameter for woven or nonwoven materials that may be incorporated in the device or through a combination of these variables.

What is claimed is:

1. A device for treatment of hollow anatomical structures comprising:
   a. a first portion;
   b. a second portion;
   c. an axial member configured to be oriented through a hollow anatomical structure and is connected to the first portion and the second portion;
   d. at least one occluding member which adjusts upon said axial member to fill the hollow anatomical structure,
   e. a first portion reinforcing element that is oriented substantially perpendicular to a longitudinal axis of the axial member;
   f. a second portion reinforcing element;
   g. a collar attached to at least one of the first and second portion reinforcing elements, and
   h. a second axial member comprising an end portion advanceable to move the first portion away from the second portion and stretch the occluding member,
   wherein the at least one of the first and second portion reinforcing elements is located between the collar and the at least one occluding member,
   wherein the at least one occluding member is configured to adjust within the hollow anatomical structure upon longitudinal translation along the axial member,
   wherein the first portion is either fixedly or slidably connected to the axial member and wherein the second portion is either fixedly or slidably connected to the axial member provided that the first portion and the second portion are not both fixedly attached to the axial member,
   wherein said at least one occluding member is collapsible by tensioning the axial member from an initial state with an initial length to a deployed state with a length shorter than said initial length and wherein said deployed occluding member is configured to conform to the geometry of a tract formed by the hollow anatomical structure and comprises a material that is bunched and has loft to aid in filling the tract formed by the hollow anatomical structure,
   wherein said first portion is an anchoring member which is expandable from an initial state with an initial diameter to a deployed state with a diameter greater than said initial diameter,
   wherein the device is adapted for catheter delivery, and
   wherein the device is adapted to be removed and redeployed.

2. The device of claim 1 wherein the first portion is in the form of a substantially planar anchoring member.

3. The device of claim 1 wherein the second portion is in the form of a fixed point or an anchoring member.

4. The device of claim 3 wherein the second portion is in the form of a substantially planar anchoring member.

5. The device of claim 1 wherein the at least one occluding member is bioabsorbable.

6. The device of claim 1 wherein said collar reduces the freedom of movement of any components which may move or slide along the axial member after deployment.

7. The device of claim 6 wherein said collar reduces the freedom of movement via chemical, mechanical or frictional means.

8. The device of claim 1, wherein the material that has loft to aid in filling the hollow anatomical structure includes a web, a mesh, a foam, or a sponge construct.

9. The device of claim 1, wherein the second axial member is a push rod.

10. A device for treatment of hollow anatomical structures comprising:
- a. a first portion in the form of a substantially planar anchoring member;
- b. a second portion;
- c. an axial member configured to be oriented through a hollow anatomical structure and is connected to the first portion and the second portion;
- d. at least one occluding member which adjusts upon said axial member to fill the hollow anatomical structure and comprises a material that is bunched and has loft to aid in filling the hollow anatomical structure,
- e. a first portion reinforcing element that is oriented substantially perpendicular to a longitudinal axis of the axial member;
- f. a second portion reinforcing element;
- g. a collar attached to at least one of the first and second portion reinforcing elements, and
- h. a second axial member comprising an end portion coupled to the first portion and advanceable to move the first portion away from the second portion and stretch the occluding member, wherein the at least one of the first and second portion reinforcing elements is located between the collar and the at least one occluding member, wherein the at least one occluding member is configured to adjust within the hollow anatomical structure upon longitudinal translation along the axial member, wherein the device is adapted to be removed and redeployed, and wherein the first portion is either fixedly or slidably connected to the axial member and wherein the second portion is either fixedly or slidably connected to the axial member provided that the first portion and the second portion are not both fixedly attached to the axial member.

11. The device of claim 10, wherein said second portion is in the form of a substantially planar anchoring member.

12. The device of claim 10, wherein said collar reduces the freedom of movement of any components which may move or slide along the axial member after deployment.

13. The device of claim 12, wherein said collar reduces the freedom of movement via chemical, mechanical or frictional means.

14. The device of claim 10, wherein the device is adapted for catheter delivery.

15. The device of claim 10, wherein said at least one occluding member is collapsible from an initial state with an initial length to a deployed state with a length shorter than said initial length and wherein said deployed occluding member is configured to conform to the geometry of a tract formed by the hollow anatomical structure.

16. The device of claim 15, wherein said first portion is expandable from an initial state with an initial diameter to a deployed state with a diameter greater than said initial diameter.

17. The device of claim 10, wherein the at least one occluding member is bioabsorbable.

18. A device for treatment of hollow anatomical structures comprising:
- a. a first portion in the form of a substantially planar anchoring member;
- b. a second portion;
- c. an axial member configured to be oriented through a hollow anatomical structure and is connected to the first portion and the second portion;
- d. at least one occluding member which adjusts upon said axial member to fill the hollow anatomical structure,
- e. a first portion reinforcing element that is oriented substantially perpendicular to a longitudinal axis of the axial member;
- f. a second portion reinforcing element;
- g. a collar attached to at least one of the first and second portion reinforcing elements, and
- h. a second axial member comprising an end portion coupled to the first portion and advanceable to move the first portion away from the second portion and stretch the occluding member, wherein the at least one of the first and second portion reinforcing elements is located between the collar and the at least one occluding member, wherein the at least one occluding member is configured to adjust within the hollow anatomical structure upon longitudinal translation along the axial member, wherein the device is adapted to be removed and redeployed, and wherein said at least one occluding member is collapsible by tensioning the axial member from an initial state with an initial length to a deployed state with a length shorter than said initial length and wherein said deployed occluding member is configured to conform to the geometry of a tract formed by the hollow anatomical structure and comprises a material that is bunched and has loft to aid in filling the tract formed by the hollow anatomical structure.

* * * * *